United States Patent
Addis

(12) 
(10) Patent No.: US 6,364,896 B1
(45) Date of Patent: *Apr. 2, 2002

(54) COMPLIANT FRAMEWORK AND METHODS OF USE

(75) Inventor: Bruce Addis, Redwood City, CA (US)

(73) Assignee: Embol-X, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/568,532

(22) Filed: May 9, 2000

Related U.S. Application Data

(63) Continuation of application No. 09/199,232, filed on Nov. 24, 1998, now Pat. No. 6,083,239.

(51) Int. Cl.[7] .............................................. A61M 29/00
(52) U.S. Cl. ...................................................... 606/200
(58) Field of Search ................................ 606/200, 198, 606/108, 159, 194

(56) References Cited

U.S. PATENT DOCUMENTS

| | | | | |
|---|---|---|---|---|
| 5,910,154 A | * | 6/1999 | Tsugita et al. | 606/200 |
| 6,083,239 A | * | 7/2000 | Addis | 606/200 |

* cited by examiner

Primary Examiner—Olik Chaudhuri
Assistant Examiner—(Vikki) Hoa B. Trinh
(74) Attorney, Agent, or Firm—Lyon & Lyon LLP

(57) ABSTRACT

An expansion mechanism which includes an elongate instrument and a plurality of struts arranged around the elongate instrument provides radial expansion of a medical device. Each strut has a first end pivotally connected to the elongate instrument and a second strut which expands radially outward. Each strut further carries a flexible line which has a proximal end and a distal end. The distal end of each line passes beyond the second end of the strut which carries it and is attached to the strut immediately adjacent the strut which carries it. Methods of using such an expansion mechanism are also disclosed, particularly to provide deployment of medical devices within a patient's blood vascular system.

10 Claims, 5 Drawing Sheets

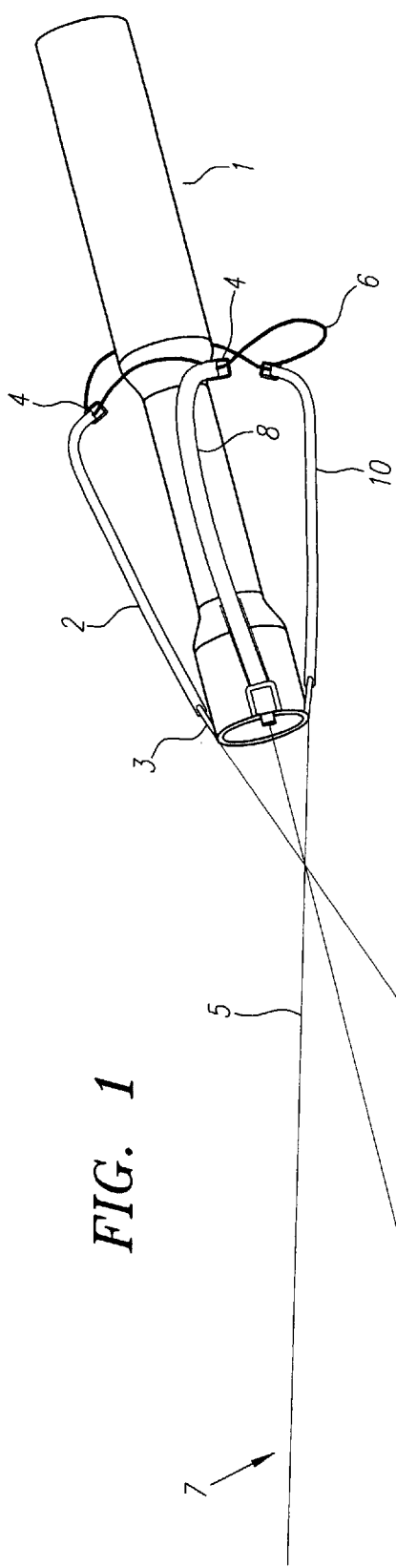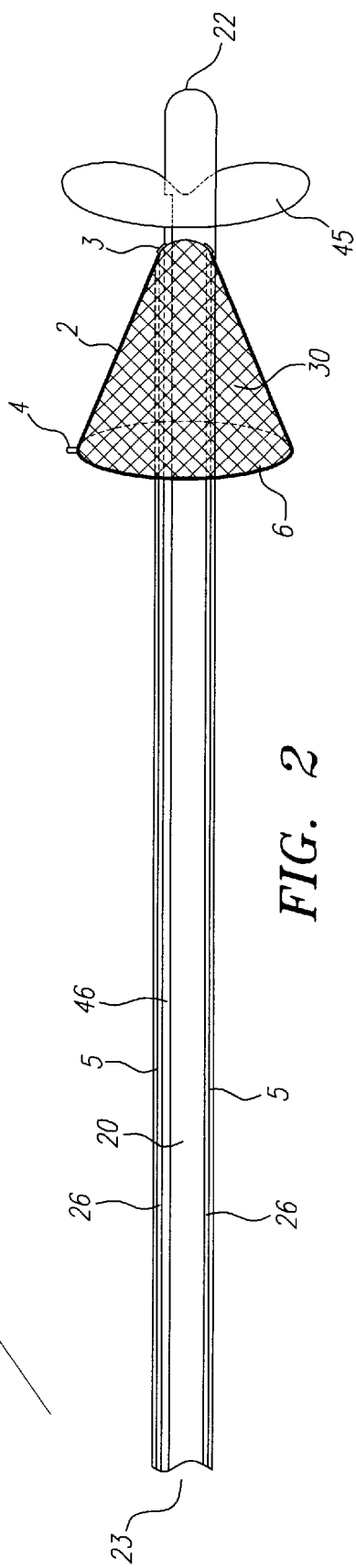

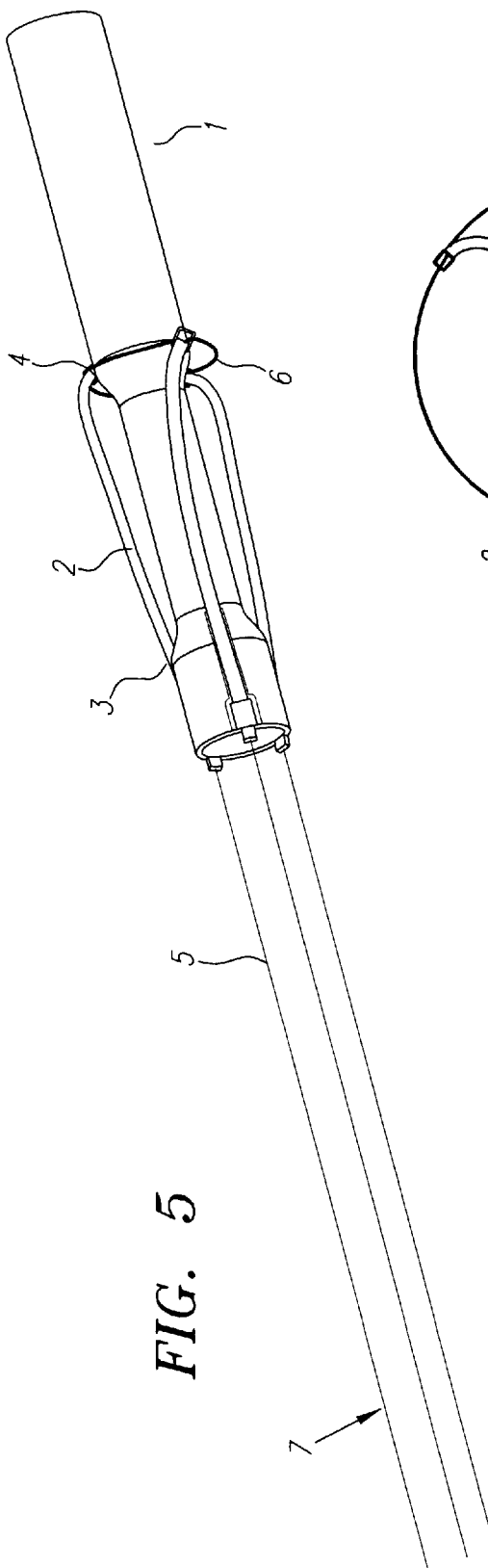
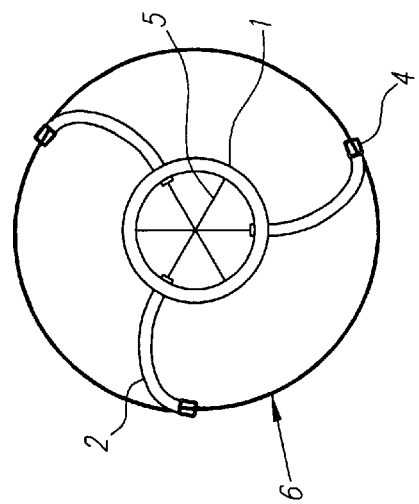
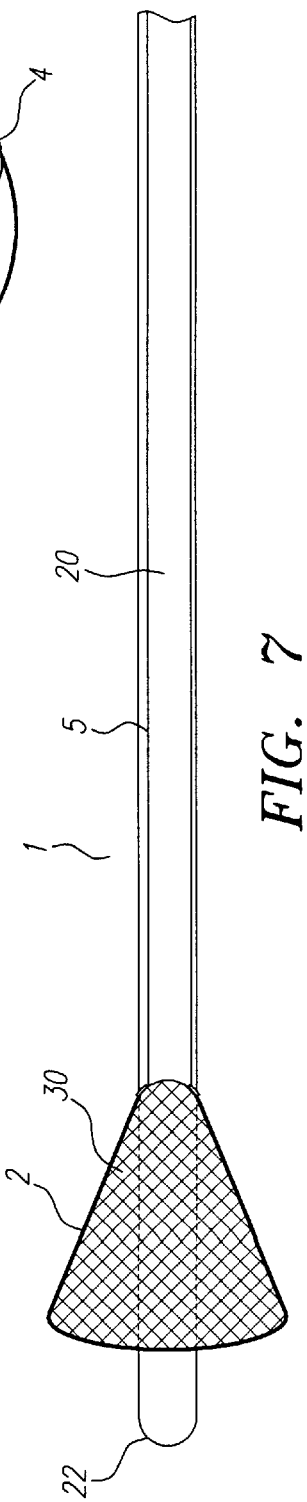
FIG. 5
FIG. 6
FIG. 7

COMPLIANT FRAMEWORK AND METHODS OF USE

The present application is a continuation of U.S. application Ser. No. 09/199,232, filed on Nov. 24, 1998, now U.S. Pat. No. 6,083,239, the contents of which are expressly incorporated herein by reference.

FIELD OF THE INVENTION

The present invention relates to an expansion mechanism for radial expansion of a medical device. More particularly, the invention relates to a compliant framework which conforms to the interior anatomy of a patients, e.g., interior blood vessel wall, with minimum gap. The framework provides structure for medical devices such as filter meshes, damming or occlusion methods, flow direction devices, and locating and measuring applications.

BACKGROUND OF THE INVENTION

During open heart surgeries, such as coronary artery bypass graft, valve repair surgeries, thoracic aneurysm repair, removal of atrial myxoma, and septal defect repairs, currently the most common method of temporarily occluding the ascending aorta utilizes a mechanical cross clamp. Aortic occlusion is needed to establish isolation of coronary circulation from the peripheral circulatory system during cardiac arrest, so that peripheral organs would not be paralyzed by cardioplegic solution. An arterial cannula is commonly inserted in a patient's aorta or femoral artery to provide return of oxygenated blood from a bypass-oxygenator machine, whereas a venous catheter is inserted into the right atrium, superior vena cava, or inferior vena cava to carry deoxygenated blood from the heart to a bypass-oxygenator machine. Other less common means of occluding the aorta include percutaneous balloon catheter occlusion, direct aortic balloon catheter (Foley) occlusion, aortic balloon occluder cannula, and an inflating diaphragm occluder (Hill—occlusion trocar).

Manipulation of ascending aorta during mechanical cross-clamping or other means of aortic occlusion often dislodges atheromatous plagues from the ascending aorta downstream to peripheral organs. Tissue debris, air, or calcium plaques may also arise from cardiac manipulation. Embolization of atheromatous plaques, tissue debris, or calcium plaques may lead to stroke, organ death or ischemia.

Devices for filtering blood have been designed to reduce a patient's peri-operative risk of peripheral embolization, thereby reducing surgical morbidity and mortality. The vast majority of these devices are designed for permanent placement in veins, in order to trap emboli destined for the lungs, e.g., Kimmell, Jr., U.S. Pat. No. 3,952,747, Cottenceau et al., U.S. Pat. No. 5,375,612, Gunther et al., U.S. Pat. No. 5,329,942, and Lefebvre, French Patent No. 2,567,405, incorporated herein by reference. Few intravascular devices are designed for arterial use, e.g., Ginsburg, U.S. Pat. No. 4,873,978, Ing. Walter Hengst GmbH & Co, German Patent DE 34 17 738, da Silva, Brazil Patent Application No. PI9301980A, and Barbut et al, U.S. Pat. No. 5,769,816, all incorporated herein by reference, have been developed to entrap arterial emboli during open-heart procedures.

The aforementioned devices all have drawbacks in that a filter or membrane to entrap emboli is deployed by means of an umbrella mechanism, thereby failing to accurately follow the rough non-uniform contour of the internal blood vessel wall. A built-in spring offers the force to bring the frame into contact with the vessel wall. The umbrella frame, however, would segment the contact, thereby only assuring a seal at each discrete arm in contact. Moreover, in using the current filter devices, an operator has little or no feel for contact between the filter mechanism and the vessel wall. Further, current designs do not permit closure which is sufficiently tight and secure to prevent release of entrapped emboli.

A need exists for devices and methods which provide contact of medical devices and vessel walls with minimum gap, give an operator a feel for the vessel wall during deployment, and permit efficient and secure closure to ensure retention of entrapped debris.

SUMMARY OF THE INVENTION

The present invention relates to an expansion mechanism for radial expansion of a medical device. More particularly, the invention provides a compliant framework which conforms to a patient's interior anatomy (such as a vessel wall) with minimum gap, provides structure for filter meshes, damming or occlusion devices, flow direction devices, locating and measuring applications, and provides a feel for the contour of vessel wall during deployment. The framework may be a metal, plastic, gel or foam.

In one embodiment, the device includes an elongate instrument which may comprise a cannula. A plurality of struts are arranged circumferentially around the elongate instrument. Each strut has two ends. The first end is pivotally connected to the elongate instrument while the second end expands radially outward. Each strut carries a wire or line having a proximal end and a distal end. The distal end of the line passes beyond the second end of the strut which carries it. The distal end of each line is attached to the strut immediately adjacent to the strut which carries it. In one embodiment, the framework has two struts and two lines. In other embodiments, the framework may have three, four, five, or six struts, and an equal number of lines arranged around the elongate instrument.

In another embodiment, the struts are mounted on a distal end of a cannula. Each strut may comprise a tubular member having a lumen and each flexible line is carried by the lumen of each tubular strut. The second end of each strut may curve toward the immediately adjacent strut.

In another embodiment, the expansion framework may be equipped with a filter mesh having two edges. A first edge of the mesh attaches circumferentially and continuously about the elongate instrument and is aligned with the first end of each strut. A second edge of the mesh may attach circumferentially to the second end of each strut and/or to a segment of each line which extends beyond the second end of each strut. The elongate instrument may comprise a blood filtration cannula. When the filter mesh is deployed inside a patient's blood vessel, as the second end of each strut expands radially outward, and the filter mesh also expands radially outward to contact the vessel wall. After embolic materials are collected from the blood onto the filter mesh, the mesh and struts are collapsed, and the cannula is removed.

In an alternative embodiment, the elongate instrument comprises a percutaneous catheter. The catheter may include a balloon occluder. The balloon occluder may be mounted proximal the struts. This embodiment provides occlusion of the blood vessel, such as aortic occlusion in open heart procedures (e.g., valve repair), in addition to providing an expansion mechanism for a filter or other medical devices. Using this construction the filter is disposed between the occluder and the heart and captures debris (which accumulates in the heart and aortic root during bypass) when the heart resumes beating and the occluder is removed. For an extensive discussion of the use of percutaneous filtration catheters of this type for prevention of stoke following valve repair surgery, the reader is referred to Jang, U.S. application Ser. No. 09/170,359, filed Oct. 13, 1998, which is incorporated herein by reference.

The methods of the present invention include deployment and expanding a portion of a medical device within a patient by using the expansion mechanism as described above. A medical device is inserted into the patient through an incision. The flexible lines are pushed distally by an operator to pay out a portion of each line beyond the end of each strut, to thereby expand the strutted portion of the device radially outward. By manipulating the lines, the operator is able to feel for the contour of an interior vessel wall, thereby minimizing the gap between the medical device and the vessel wall. To remove the medical device, the flexible lines are pulled proximally to contract the strutted portion of the device radially inward, and the device is removed from the patient.

In a preferred method, a cannula is equipped with a filter mesh disposed over the struts, and the filter mesh is expanded by pushing the flexible lines distally. During cardiac surgeries, such as valve repair surgery, the filter mesh captures embolic materials which are released from the heart or aorta. During carotid endarterectomy, the filter mesh entraps calcium and atheromatous debris from the carotid artery. After a surgical procedure is accomplished, the flexible lines are pulled and the filter mesh is contracted tightly against the elongate element. In this method, the trapped emboli are secured by the tight compliant framework during removal.

It will be understood that there are several advantages in using the framework described above. For example, (1) the filter frame and chassis allow for perfusion of fluid or blood through the center of the expansion mechanism; (2) trapped emboli are secured within a filter mesh when the wire frame is drawn closed and tight; (3) the expansion mechanism provides an operator feedback of contact between the devices and vascular wall; (4) a filter expansion mechanism may be combined with a balloon occluder and/or "direct stick" access device; and (5) the framework can adjust to a wide range of blood vessel diameter.

BRIEF DESCRIPTION OF DRAWINGS

FIG. 1 depicts an embodiment of an expansion mechanism according to the invention having its struts expanded radially outward.

FIG. 2 depicts one embodiment of a cannula having a filter mounted on its expansion framwork according to the invention.

FIG. 5 depicts an embodiment of an expansion mechanism according to the invention having its struts and flexible lines pulled tight against an elongate instrument.

FIG. 6 depicts a frontal view of the expanded mechanism shown in FIG. 1.

FIG. 7 depicts one embodiment of a percutaneous catheter having a filter mounted on its expansion framework according to the invention.

DETAILED DESCRIPTION

Figure 3:
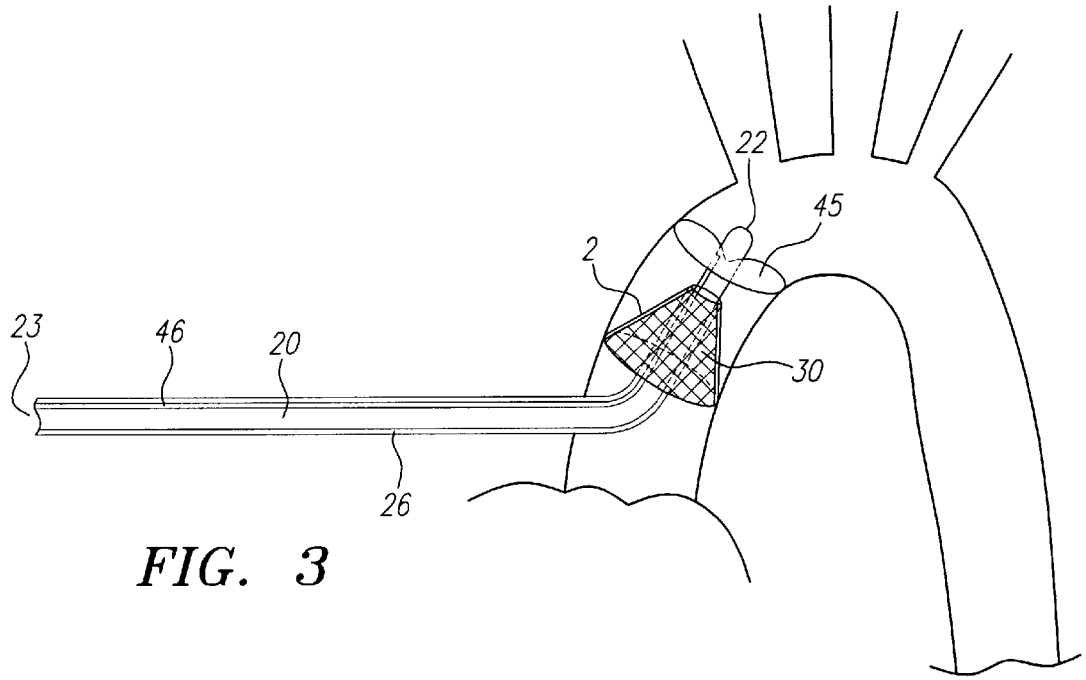
FIG. 3 depicts an aorta having the filter of FIG. 4 deployed above the aortic root.

The expansion mechanism is best employed in a vessel, such as an artery, e.g., a patient's aorta, for providing deployment of medical devices which require close approximation of the devices and the aortic wall. However, the expansion mechanism may also be suitable for deployment of medical devices such as damming or occlusion devices, and locating and measuring applications in a patient's veins or body cavities.

An embodiment of the framework is depicted in FIG. 1. This embodiment comprises struts 2, 8, and 10, each arranged circumferentially around elongate cannula 1. Other embodiments may comprise 3, 4, 5, 6, 7 or more struts. Each strut has first end 3 and second end 4. The first end is pivotally connected to cannula 1, whereas the second end expands radially outward. Flexible line 5, having proximal end 7 and distal end 6, is carried by each strut. End 6 of each line passes beyond second end 4 of each strut which carries it. End 6 is attached to the strut immediately adjacent the strut which carries it. For example, the distal end of flexible line 5, which passes beyond end 4 of strut 2, is attached to end 4 of strut 8.

In use, a medical device is operated by actuation of the framework. For example, when filter devices are needed, an expandable filter mesh is disposed about the framework as depicted in FIG. 2. Cannula 1 may be a blood filtration cannula having proximal end 23, distal end 22, and lumen 20 in between. Proximal end 23 may be adapted for attachment to a bypass-oxygenator machine. The struts are shown mounted on the distal end of the cannula. A first edge of mesh 30 is attached circumferentially about cannula 1 and aligned with end 3 of each strut, and a second edge of mesh 30 is attached circumferentially to a segment of line 6. Flexible lines 5 may be carried by additional lumen 26. In this embodiment, the cannula includes balloon occluder 45 which is mounted distal to the struts and in communication with balloon inflation lumen 46.

When the cannula of FIG. 2 is used for aortic cannulation during cardiothoracic surgeries, such as coronary artery bypass, heart valve repair, septal defect repair, resection of atrial myxoma, and thoracic aneurysm repair, the cannula is inserted into a patient's ascending aorta through an open chest incision. In minimally invasive procedures, the cannula is inserted into the aorta through a port access on the patient's chest wall. After the cannula is positioned within the aorta as depicted in FIG. 3, balloon occluder 45 is inflated to isolate the coronary circulation from the peripheral circulation. The flexible lines or wires are pushed distally to expand the mesh radially outward so that the first edge of the filter mesh is in close contact with the inner aortic wall. An operator can manipulate the flexible lines to optimally position the mesh in the aorta with minimum gap. In this embodiment, oxygenated blood may be perfused from a bypass-oxygenator through lumen 20 and distal end 22 downstream to the aorta during cardiopulmonary bypass.

Figure 4:
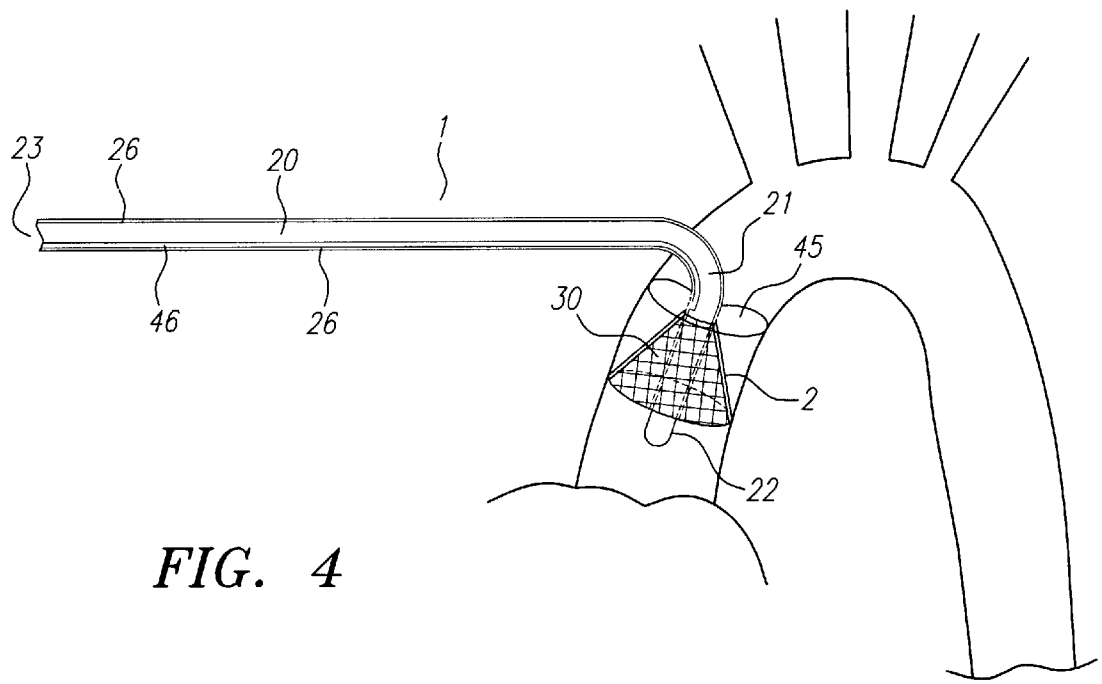
FIG. 4 depicts an alternative embodiment of the cannula with filter in FIG. 4 deployed above the aortic root.

An alternative embodiment of a blood filtration cannula according to the present invention is depicted in FIG. 4. Cannula 1 has proximal end 46, which is adapted for attachment to a bypass-oxygenator machine, distal end 22 and lumen 20. The cannula is shown inserted into the ascending aorta directed upstream in the aorta in contrast to the cannula depicted in FIG. 3, which is inserted downstream in the aorta. Balloon occluder 45 is mounted proximal to the expansion framework. Filter mesh 30 is mounted on the framework. In use, the balloon occluder is inflated through inflation lumen 46 to provide circulatory isolation, and the filter mesh is expanded to contact the interior aortic wall by pushing on flexible lines or wires. Oxygenated blood can be perfused through lumen 20 and port 21 downstream into the aorta to provide oxygenation to peripheral organs during cardiopulmonary bypass.

After a surgeon has performed surgery on the heart, the balloon occluder may be deflated. The lines are pulled to contract the mesh. Distal ends 6 of flexible lines 5 and struts 2 can be drawn closed tightly against cannula 1 as depicted in FIG. 5. In this way, the trapped embolic material is secured in the tightly contracted filter mesh, thereby avoiding unintended release during removal of the framework and mesh.

FIG. 6 depicts a frontal view of an expansion mechanism. Struts 2 are expanded radially outward from cannula 1 by pushing flexible lines 5 distally. Distal ends 6 of flexible lines 5 pass through end 4 of each strut and are attached to the strut immediately adjacent the strut which carries it.

FIG. 7 depicts an embodiment of a percutaneous catheter having a filter according to the present invention. Catheter 1 has the expansion framework mounted on distal end 22. Filter mesh is mounted struts 2 of the framework. Flexible lines 5 may be carried in lumen 20 of the catheter.

Figure 8:
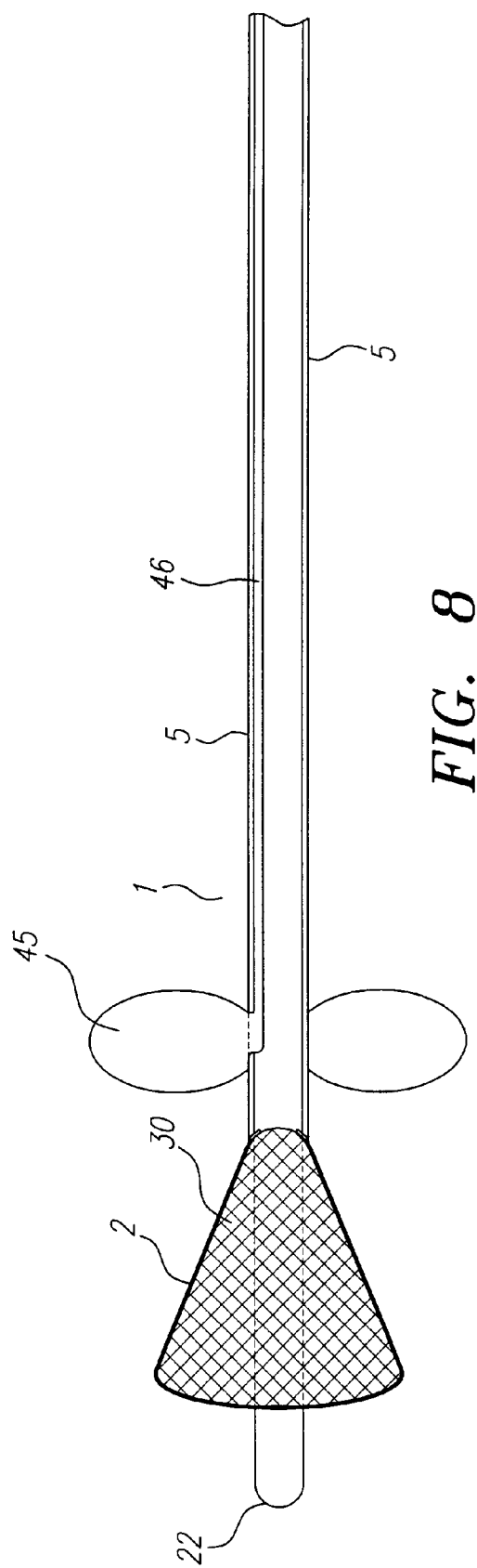
FIG. 8 depicts an alternative embodiment of a percutaneous catheter having a filter and a balloon occluder.

In certain embodiments of the percutaneous catheter depicted in FIG. 7, the catheter may further include a balloon occluder. In FIG. 8, distal end 22 of catheter 1 has filter mesh 30 mounted on struts 2 of the framework. The struts are operated by flexible lines 5 outside the catheter. Balloon occluder 45 is mounted proximal to the framework and communicates with inflation lumen 46. In other embodiments (not shown), the balloon occluder is mounted distal to the framework.

Figure 9:
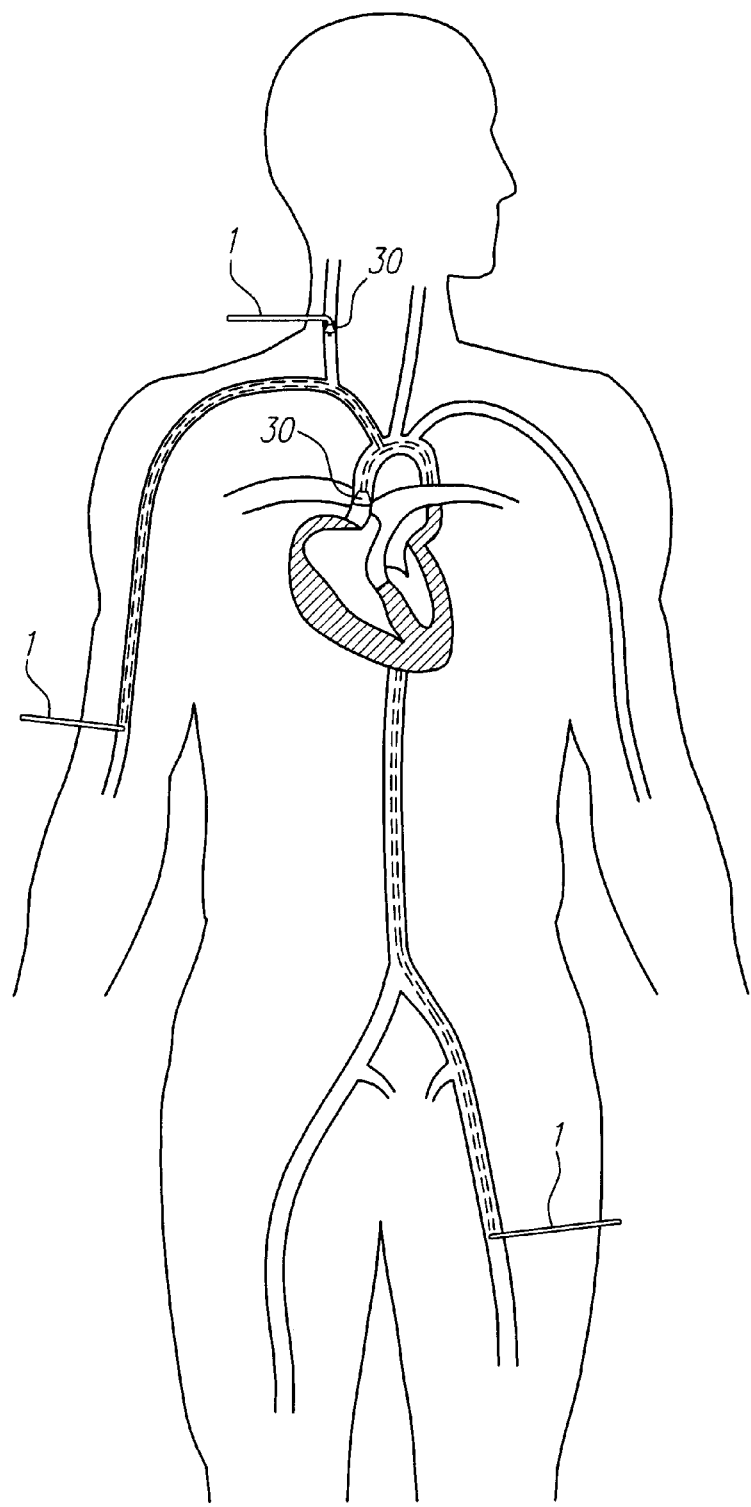
FIG. 9 depicts different entry sites for the percutaneous catheter shown in FIG. 7.

In use, the percutaneous catheter may be inserted through various cutaneous puncture sites to position above the aortic root to entrap tissue debris, calcium, and thrombi during heart valve repair surgeries. FIG. 9 depicts the percutaneous catheter of FIG. 7 entering the patient's left femoral artery and traversing the left iliac artery, descending aorta, and aortic arch to reach the ascending aorta. The distal end of the catheter is generally positioned about 4 centimeters above the aortic valves. Alternatively, the catheter can be inserted through the brachial arteries, especially in patients whose femoral arteries are not suitable for puncture. In elderly patients, the femoral arteries are often diseased, damaged or thrombosed. Catheter 1 is shown entering through the right brachial artery.

FIG. 9 also depicts the percutaneous catheter of FIG. 7 entering the patient's right carotid artery. Tissue debris, calcium plague, atheromatous material, or thrombi are often released downstream from the surgical site, thereby making stroke the major post-operative complication in carotid endarterectomy. In use, catheter 1 is inserted percutaneously into the carotid artery during endarterectomy, and filter mesh 30, mounted on the expansion framework, is positioned upstream the carotid artery. After completion of the surgery, as described in Kaganov et al., U.S. application Ser. No. 08/759,591, filed Dec. 5, 1996, incorporated herein by reference, the flexible lines or wires are pulled to tightly contract the struts and filter mesh against the catheter so that the entrapped embolic material would not be released downstream to cause cerebral infarction.

The length of the elongate instrument will generally be between 1 and 20 inches, preferably approximately 12 inches. The length of each strut will generally be between 0.2 and 2 inches, preferably approximately 1 inch. The length of the flexible lines will generally be between 4 and 25 inches, preferably approximately 15 inches. The outer diameter of the elongate instrument will generally be between 0.1 and 0.5 inches, preferably approximately 0.25 inches. The foregoing ranges are set forth solely for the purpose of illustrating typical device dimensions. The actual dimensions of a device constructed according to the principles of the present invention may obviously vary outside of the listed ranges without departing from those basic principles. Moreover, it will be understood that the dimensions of a standard cannula are well known in the art and can be used in combination with the framework disclosed herein.

Although the foregoing invention has, for purposes of clarity of understanding, been described in some detail by way of illustration and example, it will be obvious that certain changes and modifications may be practiced which will still fall within the scope of the appended claims.

What is claimed is:

1. A medical device having an expansion mechanism, comprising:

an elongate instrument having a proximal end and a distal end;

a plurality of struts arranged circumferentially around the elongate instrument, each strut having a first end pivotally connected to the elongate instrument and a second end which expands radially outward;

a plurality of flexible elongate lines, one carried by each strut, each line having a proximal end and a distal end that slideably engages the second end of the strut that carries it, the distal end of each line being attached to the strut immediately adjacent the strut that carries it; and a filter mesh disposed around the distal end of the elongate instrument, the filter mesh having an edge attached circumferentially to at least one of the plurality of struts, wherein distal advancement of the plurality of flexible elongate lines effects expansion of the struts, which in turn expands the filter mesh.

2. The medical device in claim 1, wherein the elongate instrument has a lumen positioned between the proximal end and distal end of the elongate instrument.

3. The medical device in claim 2, wherein the proximal end of the elongate instrument is adapted for attachment to a bypass-oxygenator machine.

4. The medical instrument in claim 1, wherein the filter has a second edge attached circumferentially about the elongate instrument.

5. A method for protecting a patient against embolization, comprising the steps of:

providing a medical device comprising an elongate instrument having an expansion frame comprising a plurality of struts arranged circumferentially around the instrument, each strut having an end which pivots away from the instrument, and a plurality of flexible lines, one carried by each strut, each line having a proximal end and a distal end which slideably engages the end of the strut which carries it, the distal end of each line being attached to the strut immediately adjacent the strut which carries it, the elongate instrument further including a filter mesh disposed about the expansion frame;

inserting the medical device into the patient;

pushing the flexible lines distally to expand the filter;

pulling the flexible lines proximally to contract the filter; and removing the medical device from the patient.

6. The method in claim 5, wherein the elongate instrument has a lumen extending between the proximal end and the distal end.

7. The method in claim 6, wherein the proximal end of the elongate instrument is adapted for attachment to a bypass-oxygenator machine.

8. The method in claim 5, wherein the filter mesh is disposed around the distal end of the elongate instrument and the filter mesh has an edge attached circumferentially to at least one of the plurality of struts.

9. The method in claim 7, further comprising the step of attaching the bypass-oxygenator machine to the proximal end of the elongate instrument.

10. The method in claim 9, further comprising the step of perfusing oxygenated blood through the lumen of the elongate instrument.

* * * * *